United States Patent [19]

Mullen et al.

[11] Patent Number: 5,817,463

[45] Date of Patent: Oct. 6, 1998

[54] NUCLEIC ACID PRIMERS AND PROBES FOR DETECTING *MYCOPLASMA PNEUMONIAE*

[75] Inventors: Carolyn R. Mullen, Libertyville, Ill.; Joann C. Sustachek, Racine, Wis.

[73] Assignee: Abbott Laboratories, Abbott Park, Ill.

[21] Appl. No.: 671,892

[22] Filed: Jun. 28, 1996

[51] Int. Cl.$^6$ .............................. C07H 21/04; C12Q 1/68; C12P 19/34
[52] U.S. Cl. ............................. 435/6; 435/91.2; 435/810; 536/24.32; 536/24.33; 935/8; 935/9; 935/17; 935/78
[58] Field of Search ............................... 435/6, 91.2, 810; 536/24.32, 24.33; 935/8, 78, 9, 17

[56] References Cited

U.S. PATENT DOCUMENTS 5,552,279  9/1996  Weisburg ..................................... 435/6

FOREIGN PATENT DOCUMENTS

| 0264067 | 4/1988 | European Pat. Off. . |
| 0305145 | 3/1989 | European Pat. Off. . |
| 0532167 | 3/1993 | European Pat. Off. . |
| 0576743 | 1/1994 | European Pat. Off. . |
| 9309250 | 5/1993 | WIPO . |
| 9402634 | 2/1994 | WIPO . |
| 9606949 | 3/1996 | WIPO . |
| 9707235 | 2/1997 | WIPO . |

OTHER PUBLICATIONS

Proft et al, Journal of Bacteriology (1995) 177: 3370–3378.
Colman et al, Gene (1990), vol. 87: 91–96.
Ruland et al, Journal of Bacteriology (1994) 176: 5202–5209.
Colman, S.D., et al., "Prevalence of novel repeat sequences in and around the P1 operon in the genome of *Mycoplasma pneumoniae*", *Gene*, 87:91–96 (1990).
Proft, T., et al., "The Proline–Rich P65 Protein of *Mycoplasma pneumoniae* Is a Component of the Triton X–100–Insoluble Fraction and Exhibits Size Polymorphism in the Strains M129 and FH", *Journal of Bacteriology*, 177 (12): 3370–3378 (1995).
Ruland, K., et al., "Sequence Divergence of the ORF6 Gene of *Mycoplasma penumoniae*", *Journal of Bacteriology*, 176(17):5202–5209 (1994).

*Primary Examiner*—Carla J. Myers
*Attorney, Agent, or Firm*—Paul D. Yasger

[57] ABSTRACT

Nucleic acid sequences that are useful for detecting *Mycoplasma pneumoniae* are herein provided. These sequences can be used in hybridization assays or amplification based assays designed to detect the presence of *Mycoplasma pneumoniae* in a test sample. Additionally, the sequences can be provided as part of a kit.

9 Claims, No Drawings

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( i i ) MOLECULE TYPE: genomic DNA (M. pneumoniae)

( x i ) SEQUENCE DESCRIPTION: SEQ ID NO:1:

```
CTCACCCCCT    ACACGCCCTT    TACGACACCG    CTCAATGGGG    GGCTGGATGT              50

CGTGCGCGCC    GCCCATTTAC    ACCCCTCATA    CGAACTCGTG    GACTGAAAGC             100

GGGTGGGGGA    TACCAAGTTG    GTGGCGCTGG    TCCGCTCAGC    GTTGGTCAGG             150

GTGAAATTCC    AGGAC                                                           165
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:2:

```
ACACGCCCTT    TACGACACCG                                                       20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:3:

```
TTCACCCTGA    CCAACGCTGA                                                       20
```

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 4:

```
ATTTACACCC    CTCATACGAA                                                       20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:5:

```
TTCGTATGAG    GGGTGTAAAT                                                       20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:6:

CGGTGTCGTA AAGGGCGTGT 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:7:

TCAGCGTTGG TCAGGGTGAA 20

( 2 ) INFORMATION FOR SEQ ID NO:8:

( i ) SEQUENCE CHARACTERISTICS:
        ( A ) LENGTH: 149 base pairs
        ( B ) TYPE: nucleic acid
        ( C ) STRANDEDNESS: double
        ( D ) TOPOLOGY: linear ( i i ) MOLECULE TYPE: genomic DNA (M. pneumoniae)

( x i ) SEQUENCE DESCRIPTION: SEQ ID NO:8:

CGTTGTGGCC GACCACCTCG TCTTTGCGGC CTTTAAAGCG GGCGCGGTGG 50

GGTATGATAT GACGACTGAT TCGAGCGCTT CGACCTACAA CCAAGCACTC 100

GCCTGGTCGA CCACGGCCGG GTTGGACAGT GATGGGGGGT ACAAGGCCT 149

( 2 ) INFORMATION FOR SEQ ID NO:9:

( i ) SEQUENCE CHARACTERISTICS:
        ( A ) LENGTH: 149 base pairs
        ( B ) TYPE: nucleic acid
        ( C ) STRANDEDNESS: double
        ( D ) TOPOLOGY: linear ( i i ) MOLECULE TYPE: genomic DNA (M. pneumoniae)

( x i ) SEQUENCE DESCRIPTION: SEQ ID NO:9:

CGTTGTCCAA GACCACCTCG TCTTTGCGGC CTTCAAAGCG GGCGCGGTGG 50

GGTATGATAT GACGACTGAT TCGAACGCTT CCACCAAAGA CCAAGCGCTC 100

GCCTGGTCGA CCACGGCCGG GTTGGACAGT GATGGGGGGT ACAAGGCCT 149

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:10:

GACCACCTCG TCTTTGCGGC 20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: synthetic DNA (x i) SEQUENCE DESCRIPTION: SEQ ID NO:11:

CCCCCCATCA CTGTCCAACC C  21

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: synthetic DNA (x i) SEQUENCE DESCRIPTION: SEQ ID NO:12:

GTCATATCAT ACCCCACCG  19

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: synthetic DNA (x i) SEQUENCE DESCRIPTION: SEQ ID NO:13:

GTCATATCAT ACCCCACC  18

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: synthetic DNA (x i) SEQUENCE DESCRIPTION: SEQ ID NO:14:

TCATATCATA CCCCAC  16

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: synthetic DNA (x i) SEQUENCE DESCRIPTION: SEQ ID NO:15:

GCCGCAAAGA CGAGGTGGTC  20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: synthetic DNA (x i) SEQUENCE DESCRIPTION: SEQ ID NO:16:

GGGTTGGACA GTGATGGGGG G    21

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:17:

CGGTGGGGTA TGATATGAC    19

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:18:

GGTGGGGTAT GATATGAC    18

( 2 ) INFORMATION FOR SEQ ID NO:19:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:19:

GTGGGGTATG ATATGA    16

( 2 ) INFORMATION FOR SEQ ID NO:20:

( i ) SEQUENCE CHARACTERISTICS:
        ( A ) LENGTH: 122 base pairs
        ( B ) TYPE: nucleic acid
        ( C ) STRANDEDNESS: double
        ( D ) TOPOLOGY: linear ( i i ) MOLECULE TYPE: genomic DNA (M. pneumoniae)

( x i ) SEQUENCE DESCRIPTION: SEQ ID NO:20:

CGGCTTATTA CGGCTATGGT CAGGATGGTC AAGCATATCC ACAAGACTAT    50

GCTCAAGATC CCAACCAAGC GTATTATGCC GATCCCAATG CTTATCAGGA    100

CCCAAACGCT TACACCGATC CT    122

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:21:

CGGCTATGGT CAGGATGGTC AAGC    24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:22:

AGGATCGGTG TAAGCGTTTG GGTC    24

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:23:

TTGGGATCTT GAGCATAGTC    20

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:24:

GCTTGACCAT CCTGACCATA GCCG    24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:25:

GACCCAAACG CTTACACCGA TCCT    24

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:26:

GACTATGCTC AAGATCCCAA    20

NUCLEIC ACID PRIMERS AND PROBES FOR DETECTING *MYCOPLASMA PNEUMONIAE*

FIELD OF THE INVENTION

The present invention relates to *Mycoplasma pneumoniae* and, in particular, it relates to oligonucleotides for detecting *Mycoplasma pneumoniae* in a test sample.

BACKGROUND OF THE INVENTION

Bacteria known as Mycoplasmas contain minimum intracellular organelles and are therefore some of the most simple and smallest bacteria. At least one member of the genus Mycoplasma is clinically important because of its ability to cause disease. In humans, *Mycoplasma pneumoniae* (*M. pneumoniae*) is responsible for atypical pneumonia and the symptoms of atypical pneumoniae can range from a subclinical infection to bronchopneumonia. Thus, diagnosing a *M. pneumoniae* infection based upon symptoms alone would be impractical given the range of symptoms that a patient infected with *M. pneumoniae* might display.

Currently, diagnosing a *M. pneumoniae* infection typically requires growing the organism in culture or detecting the presence of antibody against *M. pneumoniae* in a serum sample. *M. pneumoniae* is a slow growing organism and therefore, culture based methods for detecting *M. pneumoniae* may take several weeks before a result is obtained. Serological testing requires two samples from an individual suspected of being infected with *M. pneumoniae* because merely detecting antibody directed against *M. pneumoniae* is not necessarily diagnostic of a recent *M. pneumoniae* infection, but a significant increase in antibody titer may indicate a recent *M. pneumoniae* infection. Since a rise in antibody titer over time is measured, acute and convalescent serum samples are taken, but these samples are often times taken weeks apart. Hence, detecting a *M. pneumoniae* infection can be a time consuming process. Accordingly, there is a need for methods and reagents capable of detecting *M. pneumoniae* in a specific and timely manner.

SUMMARY OF THE INVENTION

The present invention provides nucleic acid sequences that can be used to specifically detect *M. pneumoniae* by using these sequences as probes and/or primers. Such primers or probes are designated SEQ ID NO 2, SEQ ID NO3, SEQ ID NO4, SEQ ID NO5, SEQ ID NO6, SEQ ID NO7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, and SEQ ID NO 26. Those skilled in the art will recognize that homologs of these sequences and combinations of these sequences can also be employed to detect *M. pneumoniae* in a test sample. Preferably, the sequences are employed in amplification reactions and can be provided in kits along with other reagents for performing an amplification reaction.

Methods provided by the present invention include hybridization assays as well as amplification based assays. Thus, according to one method, a method of detecting the presence of *M. pneumoniae* in a test sample may comprise the steps of (a) contacting the test sample with one or more of the sequences listed above, or their homologs; and (b) detecting hybridization between the above sequences and a *M. pneumoniae* target sequence as an indication of the presence of *M. pneumoniae* in the test sample.

According to another embodiment, a method for detecting the presence of *M. pneumoniae* in a test sample may comprise the steps of (a) forming a reaction mixture comprising nucleic acid amplification reagents, a test sample containing a *M. pneumoniae* target sequence, and at least one primer and one probe oligonucleotide selected from the group consisting of SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 10 and 12; SEQ ID NOs. 10 and 13; SEQ ID NOs. 10 and 14; SEQ ID NOs. 10, 11 and 12; SEQ ID NOs. 10, 11 and 13; SEQ ID NOs. 10, 11 and 14; SEQ ID NOs. 10, 11, 12, and 13; SEQ ID NOs. 10, 11, 12, 13 and 14; SEQ ID NOs. 11 and 17; SEQ ID NOs. 11 and 18; SEQ ID NOs. 11 and 19; SEQ ID NOs. 10, 11 and 17; SEQ ID NOs. 10, 11 and 18; SEQ ID NOs. 10, 11 and 19; SEQ ID NOs. 10, 11, 17, and 18; SEQ ID NOs. 10, 11, 17, 18 and 19; SEQ ID NOs. 21 and 23; SEQ ID NOs. 22 and 26; SEQ ID NOs. 21, 22 and 23; SEQ ID NOs. 21, 22 and 26; and SEQ ID NOs. 21, 22, 23 and 26. (b) subjecting the mixture to hybridization conditions to generate at least one nucleic acid sequence complementary to the target sequence; (c) hybridizing the probe to the nucleic acid sequence complementary to the target sequence, so as to form a complex comprising the probe and the complementary nucleic acid sequence; and (d) detecting the so-formed complex as an indication of the presence of *M pneumoniae* in the sample.

According to another embodiment, the invention provides kits which comprise a set of oligonucleotide primers and probes, selected from the SEQ ID NOs. listed above, and amplification reagents.

DETAILED DESCRIPTION OF THE INVENTION

As previously mentioned, the present invention provides nucleic acid sequences, methods for using these sequences and kits containing these sequences, all of which can be employed to specifically detect *M. pneumoniae*. The sequences provided are designated herein as SEQ ID NOs. 2, 3, 4, 5, 6, 7, 10, 11, 12, 13, 14, 15, 16, 17, 18, 19, 21, 22, 23, 24, 25, 26 and homologs thereof. These sequences are derived from a *M. pneumoniae* gene encoding a proline rich 65 kDa protein (P65) disclosed in Proft, T., et. al., *Journal of Bacteriology*, 177(12) p. 3370–3378 (1995); a repeat region designated SDC1 disclosed in Colman, S. D., et. al., *Gene*, 87 p. 91–96 (1990) and a repeat region designated REP 5 disclosed in Ruland, K., et. al., *Journal of Bacteriology*, 176(17) p. 5202–5209 (1994).

With respect to the sequences herein provided, the term "homologs" means those sequences sharing about 80% homology with SEQ ID NO2, SEQ ID NO3, SEQ ID NO4, SEQ ID NO5, SEQ ID NO6, SEQ ID NO7, SEQ ID NO10, SEQ ID NO11, SEQ ID NO12, SEQ ID NO13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, and SEQ ID NO 26, and more preferably those sequences that share about 90% homology with SEQ ID NO 2, SEQ ID NO 3, SEQ ID NO 4, SEQ ID NO 5, SEQ ID NO 6, SEQ ID NO 7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, and SEQ ID NO 26. Thus, sequences that share about 80% homology with the sequences provided herein and specifically hybridize with *M. pneumoniae* are intended to be within the scope of the present invention. For example, extensions of the present sequences, sequences that are shorter than the present sequences but contain a subset of the present sequences, and those sequences that deviate from the present sequences by minor base substitutions are contemplated as within the scope of the present invention.

Those skilled in the art will recognize various modifications that can be made to the sequences designated SEQ ID NO 2, SEQ ID NO 3, SEQ ID NO4, SEQ ID NO5, SEQ ID NO6, SEQ ID NO7, SEQ ID NO10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO21, SEQ ID NO 22, SEQ ID NO 23, SEQ ID NO 24, SEQ ID NO 25, and SEQ ID NO 26 without departing from their ability to specifically detect *M. pneumoniae* and share about 80% homology with these sequences. For example, 3' or 5' extensions of the present sequences with bases that are complementary to succeeding or preceding bases in either of the repeat regions (SDC1 or REP5) or the P65 gene are considered to be homologs of the present sequences when they share about 80% homology with the present sequences and specifically detect *M. pneumoniae*. Additionally, 3' or 5' extensions of present sequences with bases that are not complementary to succeeding or preceding bases in either of the repeat regions or the P65 gene that share about 80% homology with the present sequences and specifically detect *M. pneumoniae* are contemplated as within the scope of the present invention. Further, base substitutions can be made to SEQ ID NO2, SEQ ID NO3, SEQ ID NO4, SEQ ID NO5, SEQ ID NO6, SEQ ID NO 7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO21, SEQ ID NO22, SEQ ID NO23, SEQ ID NO24, SEQ ID NO 25, and SEQ ID NO 26, but these modified sequences will nevertheless maintain the ability to specifically hybridize with *M. pneumoniae* and share about 80% homology with the sequences provided herein. Sequences that are so-modified, are therefore contemplated as within the scope of the present invention. Moreover, sequences that contain about 80% of the sequences designated SEQ ID NO 2, SEQ ID NO 3, SEQ ID NO 4, SEQ ID NO 5, SEQ ID NO 6, SEQ ID NO 7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, and SEQ ID NO 26 but have bases deleted from the 3' or 5' end, are considered to be within the scope of the term homolog.

The sequences disclosed herein, as well as their homologs, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

Generally, the sequences provided herein can be employed to detect the presence of *M. pneumoniae* in a test sample by contacting a test sample with at least one of the sequences provided herein under hybridizing conditions and detecting hybridization between the *M. pneumoniae* target sequence and at least one of the sequences designated herein as SEQ ID NO 2, SEQ ID NO 3, SEQ ID NO 4, SEQ ID NO 5, SEQ ID NO6, SEQ ID NO7, SEQ ID NO10, SEQ ID NO11, SEQ ID NO12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, and SEQ ID NO 26. Several well known methods for detecting hybridization can be employed according to the present invention and may include, for example, the use of gels and stains or detecting a label associated with one or more of the sequences provided herein after performing, for example, a dot blot or amplification reaction.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like.

A "target sequence" as used herein means a nucleic acid sequence that is detected, amplified, both amplified and detected or otherwise is complementary to one of the sequences herein provided. Thus, a target sequence generally will be at least about 80% complementary with the sequences provided herein. Additionally, while the term target sequence is sometimes referred to as single stranded, those skilled in the art will recognize that the target sequence may actually be double stranded.

"Hybridization" or "hybridizing" conditions are defined generally as conditions which promote annealing between complementary nucleic acid sequences or annealing and extension of one or more nucleic acid sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

The sequences provided herein also can be used as amplification primers or probes according to amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930 all of which are herein incorporated by reference.

According to a preferred embodiment, the sequences are employed in the "oligonucleotide hybridization PCR" (variably referred to herein as "OH PCR") amplification reaction as described in U.S. patent application Ser. No. 08/514,704, filed Aug. 14, 1995, that is herein incorporated by reference. Briefly, the reagents employed in the preferred method comprise at least one amplification primer and at least one internal hybridization probe, as well as other reagents for performing an amplification reaction.

The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

"Other reagents for performing an amplification reaction" or "nucleic acid amplification reagents" include reagents which are well known and may include, but are not limited to, an enzyme having polymerase activity, enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

The preferred method generally comprises the steps of (a) forming a reaction mixture comprising nucleic acid amplification reagents, at least one hybridization probe, at least one amplification primer and a test sample suspected of containing a target sequence; (b) subjecting the mixture to hybridization conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of *M. pneumoniae* in the sample. It will be understood that step (b) of the above method can be repeated several times prior to step (c) by thermal cycling the reaction mixture as is well known in the art.

According to the above method, it is preferable to select primers, probes and reaction conditions such that the probe sequence has a lower melt temperature than the primer sequences so that upon placing the reaction mixture under hybridization conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

Upon formation of the copy sequence/probe hybrids, the differential labels (i.e. capture and detection labels) on the copy sequence and probe sequence can be used to separate and detect such hybrids. Preferably, detection is performed according to the protocols used by the commercially available Abbott LCx® instrumentation Abbott Laboratories; Abbott Park, Ill.).

Thus, keeping the preferred method in mind, the sequences of the present invention are preferably provided in groups of at least two different sequences (i.e. at least one primer sequence and at least one probe sequence complementary to the extension product of the primer). Hence, SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 10 and 12; SEQ ID NOs. 10 and 13; SEQ ID NOs. 10 and 14; SEQ ID NOs. 10, 11 and 12; SEQ ID NOs. 10, 11 and 13; SEQ ID NOs. 10, 11 and 14; SEQ ID NOs. 10, 11, 12, and 13; SEQ ID NOs. 10, 11, 12, 13 and 14; SEQ ID Nos. 11 and 17; SEQ ID NOs. 11 and 18; SEQ ID NOs. 11 and 19; SEQ ID NOs. 10, 11 and 17; SEQ ID NOs. 10, 11 and 18; SEQ ID NOs. 10, 11 and 19; SEQ ID NOs. 10, 11, 17, and 18; SEQ ID NOs. 10, 11, 17, 18 and 19; SEQ ID NOs. 21 and 23; SEQ ID NOs. 22 and 26; SEQ ID NOs. 21, 22 and 23; SEQ ID NOs. 21, 22 and 26; and SEQ ID NOs. ,21, 22, 23 and 26; or homologs of these sequences are preferably provided together.

The sequences of the present invention can be provided as part of a kit useful for detecting *M. pneumoniae*. The kits comprise one or more suitable containers containing one or more sequences according to the present invention, an enzyme having polymerase activity, and deoxynucleotide triphosphates. Typically, at least one sequence bears a label, but detection is possible without this.

The following examples are provided to further illustrate the present invention and not intended to limit the invention.

EXAMPLES

The following examples demonstrate *M. pneumoniae* detection using the DNA oligomer primers and probes herein provided. These DNA primers and probes are identified as SEQUENCE ID NO. 2, SEQUENCE ID NO. 3, SEQUENCE ID NO. 4, SEQUENCE ID NO. 5, SEQUENCE ID NO. 10, SEQUENCE ID NO. 11, SEQUENCE ID NO. 12, SEQUENCE ID NO. 13, SEQUENCE ID NO. 14, SEQUENCE ID NO. 21, SEQUENCE ID NO. 22, and SEQUENCE ID NO. 23. SEQUENCE ID NOs. 2, 3, 4 and 5 are specific for the multicopy repetitive element, Rep 5, region in the ORF6 gene of *M. pneumoniae*. A portion of the Rep 5 sequence is designated as SEQ ID NO. 1. SEQUENCE ID NOs. 10, 11, 12, 13 and 14 are specific for the multicopy repetitive SDC1 element of *M. pneumoniae*. Regions of the SDC1 repeat element from *M. pneumoniae* strains M129 and FH are designated herein as SEQ ID NO. 8 and SEQ ID NO. 9 respectively. SEQUENCE ID NOs. 21, 22 and 23 are specific for the gene encoding the proline-rich p65 protein of *M. pneumoniae*. A portion of this gene is designated herein as SEQ ID NO. 20. In the following examples, SEQUENCE ID NO. 2 and SEQUENCE ID NO. 3 are used as *M. pneumoniae* amplification primers specific for the Rep 5 region. SEQUENCE ID NO. 4 and SEQUENCE ID NO. 5 are used as internal hybridization probes for the Rep 5 amplification product. SEQUENCE ID NO 10 and SEQUENCE ID NO 11 are used as *M. pneumoniae* amplification primers specific for the SDC1 region and SEQUENCE ID NO 12, 13 and 14 are used as internal hybridization probes for the SDC1 amplification product. SEQUENCE ID NO. 21 and SEQUENCE ID NO. 22 are used as *M. pneumoniae* amplification primers specific for the p65 region and SEQUENCE ID NO. 23 is used as an internal hybridization probe for the p65 amplification product.

Example 1

Preparation of *M. pneumoniae* Primers and Probes

A. Rep 5 Primers and Probes Target-specific primers and probes were designed to detect the *M. pneumoniae* Rep 5 target sequence by oligonucleotide hybridization PCR. These primers were SEQUENCE ID NO. 2 and SEQUENCE ID NO. 3. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

The detection probes were designed to hybridize with the amplified *M. pneumoniae* Rep 5 target sequence by oligonucleotide hybridization. These probes are SEQUENCE ID NO 4 and SEQUENCE ID NO 5. The probe sequences were synthesized using standard oligonucleotide synthesis methodology and haptenated with 2 carbazoles at the 5' end using standard cyanoethyl phosphoramidite coupling chemistry as described in U.S. Pat. No. 5,464,746 (herein incorporated by reference), and blocked with phosphate at the 3' end. Reactivity was assessed against a known standard of *M. pneumoniae* DNA.

B. SDC1 Primers and Probes Target-specific primers and probes were designed to detect the *M. pneumoniae* SDC1 target sequence by oligonucleotide hybridization PCR. These primers were SEQUENCE ID NO. 10 and SEQUENCE ID NO.11. Primer sequences were synthesized using standard oligonucleotide synthesis methodology and haptenated with adamantane at their 5' ends using standard cyanoethyl phosphoramidite coupling chemistry (as above).

The detection probes were designed to hybridize with the amplified *M. pneumoniae* SDC1 target sequence by oligonucleotide hybridization. These probes are SEQUENCE ID NOs. 12, 13 and 14. The probe sequences were synthesized using standard oligonucleotide synthesis methodology and haptenated with 2 carbazoles at the 5' end using standard cyanoethyl phosphoramidite coupling chemistry (as above), and blocked with phosphate at the 3' end. Reactivity was assessed against a known standard of *M. pneumoniae* DNA.

C. p65 Primers and Probe Target-specific primers and probes were designed to detect the *M. pneumoniae* p65 target sequence by oligonucleotide hybridization PCR. These primers were SEQUENCE ID NO. 21 and SEQUENCE ID NO. 22. Primer sequences were synthesized using standard oligonucleotide synthesis methodology and haptenated with adamantane at their 5' ends using standard cyanoethyl phosphoramidite coupling chemistry (as above).

The detection probe was designed to hybridize with the amplified *M. pneumoniae* p65 target sequence by oligonucleotide hybridization. This probe is SEQUENCE ID NO. 23. The probe sequence was synthesized using standard oligonucleotide synthesis methodology and haptenated with 2 carbazoles at the 5' end using standard cyanoethyl phosphoramidite coupling chemistry and blocked with phosphate at the 3' end (as above). Reactivity was assessed against a known standard of *M. pneumoniae* DNA.

Example 2

Sensitivity of *M. pneumoniae* Detection

The *M. pneumoniae* standards used were obtained from American Type Culture Collection, Rockville, Md.; the FH strain of *M. pneumoniae* was from ATCC #15531 and the M129 strain of *M. pneumoniae* was from ATCC #29342. ATCC #15293 (*M. pneumoniae,* strain not indicated) was used in instances where knowledge of the particular strain was not necessary.

DNA was extracted and purified from the cell cultures by lysing the cells with detergent, digesting RNA and proteins with RNase and Proteinase K respectively, heating to inactivate, then isolating DNA using phenol/chloroform extraction and ethanol precipitation. DNA was quantitated by taking an absorbance reading at 260 nm using a spectrophotometer.

A. M. pneumoniae Rep 5 detection Dilutions of the DNA purified from the M. pneumoniae standard cell lines were PCR amplified and detected using the REP 5 primers (SEQ ID NOs. 2 and 3) with each of the REP 5 detection probes (SEQ ID NO. 4 or SEQ ID NO. 5) described in Example 1. The detection probes were used in separate reactions to detect the amplification products produced by the REP 5 primers. Taq polymerase was used at a concentration of 2.5 units and the final concentration of the nucleotides was 0.2 mM each in a total reaction volume of 0.2 ml. PCR extension was performed using 10× PCR buffer (Perkin Elmer, Foster City, Calif.) which consists of 100 mM Tris-HCl, pH 8.3, 500 mM KCl, at a final concentration of 1×. The reaction mixtures containing 5 nM of SEQ ID NO. 4 used primers at a concentration of 0.2 μM each, with a final concentration of 1.5 mM $MgCl_2$. The reaction mixtures containing 10 nM of SEQ ID NO. 5 used primers at a concentration on 0.5 μM each, with a final concentration of 1.0 mM $MgCl_2$. Testing was done in triplicate with calf thymus DNA as a negative control.

Reaction mixtures were amplified in a Perkin-Elmer 480 Thermal Cycler. For reaction mixtures employing SEQ ID NO. 4 as a probe, the following cycling conditions were used: 95° C. for 5 minutes followed by cycling at 95° C. for 1 minute/68° C. for 1 minute/72° C. for 1 minute for 40 cycles. For reaction mixtures employing SEQ ID NO. 5 as a probe, the following cycling conditions were used: 95° C. for 5 minutes followed by cycling at 95° C. for 1 minute/65° C. for 1 minute/72° C. for 1 minute for 40 cycles. After the reaction mixtures were thermal cycled, the mixtures were maintained at 97° C. for 5 minutes and probe oligo hybridization was accomplished by lowering the temperature to 15° C. Following probe hybridization, samples were either assayed immediately or held at 2° C.–25° C., for up to 24 hours before being tested.

Reaction products were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The average values from this experiment (calculated as counts/second/second; c/s/s) are presented in TABLE 1 and show detection of both strains of M. pneumoniae by both probe sequences at concentrations as low as 1 molecule of M. pneumoniae genomic DNA.

TABLE 1

| Sample | Molecules of M. pneumoniae Genomic DNA | Probe SEQ ID NO 4 LCx ® rate (c/s/s) | Probe SEQ ID NO 5 LCx ® rate (c/s/s) |
|---|---|---|---|
| M. pneumoniae, FH | 100 | 1285 | 1379 |
| " | 10 | 1149 | 1321 |
| " | 1 | 708 | 1099 |
| Negative Control | 0 | 16 | 20 |
| M. pneumoniae, M129 | 1000 | 1370 | 1448 |
| " | 100 | 1358 | 1382 |
| " | 10 | 1175 | 1238 |

TABLE 1-continued

| Sample | Molecules of M. pneumoniae Genomic DNA | Probe SEQ ID NO 4 LCx ® rate (c/s/s) | Probe SEQ ID NO 5 LCx ® rate (c/s/s) |
|---|---|---|---|
| " | 1 | 1072 | 1110 |
| Negative Control | 0 | 18 | 18 |

Additional testing was performed comparing dilutions of M. pneumoniae strain M129 in either human placental DNA (tested in triplicate) or calf thymus DNA (tested in duplicate). Oligonucleotide hybridization PCR with SEQ ID NOs. 2, 3, 4, and 5 was performed with the individual probes as above. The results, shown as averages in Table 2, again indicate detection of M. pneumoniae at concentrations as low as 1 molecule M. pneumoniae genomic DNA.

TABLE 2

| Molecules of M. pneumoniae Genomic DNA | Background DNA | Probe SEQ ID NO 4 LCx ® rate (c/s/s) | Probe SEQ ID NO 5 LCx ® rate (c/s/s) |
|---|---|---|---|
| 1000 | Human placental | 1468 | 1430 |
| 100 | " | 1498 | 1401 |
| 10 | " | 1531 | 1145 |
| 1 | " | 1254 | 611 |
| 0 | " | 20 | 20 |
| 1000 | Calf Thymus | 1486 | 1486 |
| 100 | " | 1500 | 1434 |
| 10 | " | 1541 | 1312 |
| 1 | " | 1167 | 1000 |
| 0 | " | 21 | 21 |

B. M. pneumoniae SDC1 detection Dilutions of the DNA purified from the FH strain of the M. pneumoniae standard cell line were PCR amplified and detected using the SDC1 primers (SEQ ID NOs. 10 and 11) with each of the SDC1 detection probes (SEQ ID NOs. 12, 13 or 14) in separate reactions. Testing was done in duplicate. Taq polymerase was used at a concentration of 2.5 units and the final concentration of the nucleotides was 0.2 mM each in a total reaction volume of 0.2 ml. PCR extension was performed using 10× PCR buffer (Perkin Elmer, Foster City, Calif.) which consists of 100 mM Tris-HCl, pH 8.3, 500 mM KCl, at a final concentration of 1×. The primers were used at a concentration of 0.25 μM each, and probes were used at a concentration of 10 nM. The final concentration of $MgCl_2$ was 1 mM.

Reaction mixtures were amplified in a Perkin-Elmer 480 Thermal Cycler under the following cycling conditions: 95° C. for 5 minutes followed by cycling at 95° C. for 1 minute/65° C. for 1 minute/72° C. for 1 minute for 40 cycles. After maintaining the reaction mixture at 97° C. for 5 minutes, probe oligo hybridization was accomplished by lowering the temperature to 15° C. Following probe hybridization, samples were either assayed immediately or held at 2° C.–25° C. for up to 24 hours before being tested.

Reaction products were detected on the Abbott LCx® system as above in Example 2.A. Results, shown in Table 3 as averages of the duplicate values indicate detection of M. pneumoniae by all 3 probe sequences at concentrations as low as 1 molecule of M. pneumoniae genomic DNA.

TABLE 3

| Molecules of M. pneumoniae DNA | Probe SEQ ID NO 12 LCx ® rate (c/s/s) | Probe SEQ ID NO 13 LCx ® rate (c/s/s) | Probe SEQ ID NO 14 LCx ® rate (c/s/s) |
| --- | --- | --- | --- |
| 100 | 1807 | 1656 | 1181 |
| 10 | 1638 | 1485 | 656 |
| 1 | 495 | 619 | 147 |
| 0 (Neg. Control) | 96 | 52 | 32 |

Dilutions of both strains of M. pneumoniae DNA were then tested using the SEQ ID NO 12 probe only. In this experiment primers were used at a concentration of 0.35 µM each, probes were used at a concentration of 12.5 nM and the final concentration of $MgCl_2$ was 1.5 mM. Samples were tested in replicates of four, and calf thymus DNA was used as a negative control (NC).

Reaction mixtures were amplified in a Perkin-Elmer 480 Thermal Cycler under the following cycling conditions: 95° C. for 2 minutes followed by cycling at 95° C. for 1 minute/67° C. for 1 minute/72° C. for 1 minute for 40 cycles. Probe hybridization and detection was accomplished on the Abbott LCx® system as in Example 2.A. The average values from this experiment are presented in TABLE 4 and show detection of both strains of M. pneumoniae at concentrations as low as 1 molecule of M. pneumoniae genomic DNA.

TABLE 4

| Sample | Molecules of M. pneumoniae DNA | Probe SEQ ID NO 12 LCx ® rate (c/s/s) |
| --- | --- | --- |
| M. pneumoniae, M129 | 1000 | 1795 |
| " | 100 | 1792 |
| " | 10 | 1568 |
| " | 1 | 982 |
| M. pneumoniae, FH | 1 | 892 |
| calf thymus DNA NC | 0 | 18 |

C. M. pneumoniae detection with p65 primers and probes. Dilutions of both strains of M. pneumoniae DNA were PCR amplified and detected using the p65 primers (SEQ ID NOs. 21 and 22) and the p65 detection probe (SEQ ID NO. 23) described in Example 1. Taq polymerase was used at a concentration of 2.5 units and the final concentration of the nucleotides was 0.2 mM each in a total reaction volume of 0.2 ml. PCR extension was performed using 10× PCR buffer (Perkin Elmer, Foster City, Calif.) which consists of 100 mM Tris-HCl, pH 8.3, 500 mM KCl, at a final concentration of 1×. Primers were used at a concentration of 0.35 µM each, probes were used at a concentration of 12.5 nM and the final concentration of $MgCl_2$ was 1.5 mM. Samples were tested in replicates of four, and calf thymus DNA was used as a negative control (NC).

Reaction mixtures were amplified in a Perkin-Elmer 480 Thermal Cycler under the following cycling conditions: 95° C. for 5 minutes followed by cycling at 95° C. for 1 minute/67° C. for 1 minute/72° C. for 1 minute for 40 cycles. After maintaining the reaction mixture at 97° C. for 5 minutes, probe oligo hybridization was accomplished by lowering the temperature to 15° C. Following probe hybridization, samples were either assayed immediately or held at 2° C.–25° C. for up to 24 hours before being tested.

Reaction products were detected on the Abbott LCx® system as in Example 2.A. Results, with averages shown in Table 5, show detection of both strains of M. pneumoniae at concentrations as low as 10 molecules of M. pneumoniae genomic DNA.

TABLE 5

| Sample | Molecules of M. pneumoniae DNA | p65 LCx ® rate (c/s/s) |
| --- | --- | --- |
| M. pneumoniae, M129 | 1000 | 1555 |
| " | 100 | 1486 |
| " | 10 | 1323 |
| M. pneumoniae, FH | 100 | 1545 |
| " | 10 | 1233 |
| calf thymus DNA (NC) | 0 | 17 |

Additional testing was performed with both strains in triplicate at concentrations below 20 molecules of DNA. Calf thymus DNA was used as the negative control (NC) and tested in quadruplicate. The results shown in Table 6 indicate detection of M. pneumoniae at concentrations as low as 5 molecules of M. pneumoniae genomic DNA.

TABLE 6

| Sample | Molecules of M. pneumoniae DNA | p65 LCx ® rate (c/s/s) |
| --- | --- | --- |
| M. pneumoniae, M129 | 10 | 1423 |
| " | 5 | 1435 |
| " | 1 | 25* |
| M. pneumoniae, FH | 10 | 1527 |
| " | 5 | 1200* |
| " | 1 | 25* |
| calf thymus DNA (NC) | 0 | 34 |

*One aberrant value not included in calculation of average.

Example 3

Specificity of M. pneumoniae Detection

Three other members of the genus Mycoplasma, M. genitalium, M. orale and M. salivarium (ATCC #33530, 23714 and 23064 respectively) were purchased from Advanced Biotechnologies, Inc. (Columbia, Md.). Organisms were quantified by titration and plating out to determine the CFU titer (the number of colony forming units/ml). They were then lysed and diluted to $10^3$ to $10^5$ CFU/reaction. Alternatively DNA was extracted, purified and quantified as in Example 2., except that RNase digestion was done following DNA extraction and purification, with phenol/chloroform extraction and ethanol precipitation repeated after RNase digestion. Samples were then diluted to $10^6$ to $10^8$ molecules of DNA/reaction and assayed side by side with the purified M. pneumoniae DNA from Example 2., as described below.

A. Specific detection of M. pneumoniae using the REP 5 primers and probes The REP 5 primers (SEQ ID NO 2 and SEQ ID NO 3) and REP 5 detection probes (SEQ ID NO 4 or SEQUENCE ID NO 5) described in Example 1 were used to amplify and detect four samples from the genus Mycoplasma by the method previously described in Example 2.A. above for the SEQ ID NO. 5 probe. Samples were tested in duplicate with water as a negative control. The data from this experiment is presented in TABLE 7 and shows specific amplification and detection of M. pneumoniae only, with the 3 other Mycoplasma genus samples being non-reactive.

TABLE 7

| Sample | Concentration/Reaction | Probe SEQ ID NO 4 LCx ® rate (c/s/s) | Probe SEQ ID NO 5 LCx ® rate (c/s/s) |
|---|---|---|---|
| Water (Neg. Ctl.) | | 15 | 19 |
| M. genitalium | $10^5$ CFU | 17 | 20 |
| " | $10^4$ CFU | 13 | 20 |
| " | $10^3$ CFU | 14 | 19 |
| M. orale | $10^5$ CFU | 14 | 20 |
| " | $10^4$ CFU | 14 | 19 |
| " | $10^3$ CFU | 13 | 18 |
| M. salivarium | $10^5$ CFU | 16 | 19 |
| " | $10^4$ CFU | 13 | 19 |
| " | $10^3$ CFU | 13 | 19 |
| M. pneumoniae | $10^4$ mol of DNA | 1491 | 1812 |
| M. genitalium | $10^8$ mol of DNA | 17 | 22 |
| " | $10^7$ mol of DNA | 16 | 19 |
| " | $10^6$ mol of DNA | 15 | 18 |
| M. orale | $10^8$ mol of DNA | 13 | 17 |
| " | $10^7$ mol of DNA | 47 | 17 |
| " | $10^6$ mol of DNA | 18 | 18 |
| M. salivarium | $10^8$ mol of DNA | 18 | 25 |
| " | $10^7$ mol of DNA | 14 | 19 |
| " | $10^6$ mol of DNA | 13 | 17 |
| M. pneumoniae | $10^3$ mol of DNA | 1463 | 1756 |

(CFU = colony forming units; mol of DNA = molecules of DNA)

B. Specific detection of *M. pneumoniae* using SDC1 primers and probes The SDC1 primers (SEQ ID NO 10 and SEQ ID NO 11) and SDC1 detection probe (SEQ ID NO 14) described in Example 1 were used to amplify and detect four samples from the genus Mycoplasma by the method described in Example 2.B. Samples were tested in triplicate. The data from this experiment is presented in TABLE 8 and shows specific amplification and detection of *M. pneumoniae* only, with the 3 other Mycoplasma genus samples being non-reactive.

TABLE 8

| Sample | Molecules of Mycoplasma DNA | Probe SEQ ID NO 14 LCx ® rate (c/s/s) |
|---|---|---|
| Negative Control | 0 | 33 |
| M. genitalium | $10^8$ | 21 |
| M. orale | $10^8$ | 30 |
| M. salivarium | $10^8$ | 23 |
| M. pneumoniae, FH | $10^4$ | 1082 |

C. Specific detection of *M. pneumoniae* using p65 primers and probes The p65 primers (SEQ ID NO 21 and SEQ ID NO 22) and p65 detection probe (SEQ ID NO 23) described in Example 1 were used to amplify and detect four samples from the genus Mycoplasma by the method described in Example 2.C. except that the probe concentration was 14 nM. Samples were tested in triplicate. The data from this experiment is presented in TABLE 9 and shows specific amplification and detection of *M. pneumoniae* only, with the 3 other Mycoplasma genus samples being non-reactive.

TABLE 9

| Sample | Molecules of Mycoplasma DNA | p65 LCx ® rate (c/s/s) |
|---|---|---|
| Negative Control | 0 | 21 |
| M. genitalium | $10^7$ | 19 |
| M. orale | $10^7$ | 20 |
| M. salivarium | $10^7$ | 24 |
| M. pneumoniae, M129 | 5 | 1194 |

TABLE 9-continued

| Sample | Molecules of Mycoplasma DNA | p65 LCx ® rate (c/s/s) |
|---|---|---|
| " | 10 | 1380 |
| " | 100 | 1388 |
| " | 1000 | 1426 |

Example 4

Specificity of *M. pneumoniae* Rep 5 Primers and Probe

A panel of organisms (Table 10) which had been quantified by titration and plating out to determine the CFU titer (the number of colony forming units/ml) was obtained from the ATCC. DNA was isolated from the organisms in the panel using the QIAgen nucleic acid purification method (QIAgen, Inc., Chatsworth, Calif.) and amplified and detected using the REP 5 primers (SEQ ID NO 2 and SEQ ID NO 3) and REP 5 detection probe (SEQ ID NO 5) described in Example 1 by the Rep 5 method described for the SEQ ID NO 5 probe in Example 2.A. above, except that the final concentration of $MgCl_2$ was 1.5 mM. Purified *M. pneumoniae* from the FH strain was used as a positive control and calf thymus DNA was used as a negative control (NC); all controls were tested in replicates of twelve. The data from this experiment is presented in TABLE 10 and shows specific amplification and detection of *M. pneumoniae* only, with all other organisms being non-reactive.

TABLE 10

| Organism | ATCC No. | Concentration/Reaction | Rep 5 LCx ® rate (c/s/s) |
|---|---|---|---|
| Nocardia asteroides | 23825 | 8.9 × 10e5 CFU | 24.7 |
| Nocardia brasiliensis | 19296 | 2.1 × 10e7 CFU | 21.2 |
| Nocardia otitidiscaviarum | 14629 | 7.7 × 10e6 CFU | 24.9 |
| Corynebacterium kutscherii | 15677 | 4.9 × 10e7 CFU | 23.1 |
| Dermatophilus congolensis | 14637 | 2.0 × 10e6 CFU | 25.1 |
| Rhodococcus erythropolis | 4227 | 6.5 × 10e6 CFU | 25.8 |
| N. dassonvillei subspecies dassonvillei | 21944 | 2.1 × 10e7 CFU | 27.8 |
| Streptococcus mitis | 9811 | 3.7 × 10e6 CFU | 22.4 |
| Streptococcus pneumoniae | 6303 | 5.8 × 10e5 CFU | 21.5 |
| Nocardia asteroides | 19247 | 7.6 × 10e6 CFU | 21.8 |
| Pseudomonas aeruginosa | 142 | 3.8 × 10e6 CFU | 23.3 |
| Candida albicans | 18304 | 1.2 × 10e6 CFU | 23.3 |
| Lactobacillus catenaformis | 25536 | 1.7 × 10e6 CFU | 21.6 |
| Listeria monocytogenes | 984 | 7.0 × 10e5 CFU | 20.6 |
| Legionella micdadei | 33204 | 1.5 × 10e5 CFU | 24.1 |
| Streptomyces griseus subspecies griseus | 3343 | 1.9 × 10e6 CFU | 22.7 |
| Corynebacterium pseudotuberculosis | 19410 | 3.5 × 10e7 CFU | 21.9 |
| Corynebacterium diphtheriae | 296 | 2.3 × 10e7 CFU | 25.9 |
| Proprionibacterium acnes | 6921 | 5.4 × 10e6 CFU | 24.2 |
| Achromobacter sp. | 14648 | 2.7 × 10e6 CFU | 25.2 |
| Mycobacteria pneumoniae | 15293 | 4.4 × 10e8 CFU | 1535.5 |
| B. thetaiotamicron | 29148 | 5.7 × 10e6 CFU | 25.8 |
| Actnomyces israeli | 10048 | 2.1 × 10e6 CFU | 21.4 |

TABLE 10-continued

| Organism | ATCC No. | Concentration/ Reaction | Rep 5 LCx ® rate (c/s/s) |
|---|---|---|---|
| serotype 1 | | | |
| Staphylococcus aureus protein A | 12598 | 7.8 × 10e7 CFU | 26.0 |
| Acinetobacter calcoaceticus (A. baumanii) | 14987 | 2.5 × 10e6 CFU | 24.9 |
| Clostridium perfringens | 9081 | 2.3 × 10e6 CFU | 22.8 |
| Enterococcus faecalis | 376 | 9.0 × 10e6 CFU | 23.3 |
| Salmonella cholerasuis serotype typhi | 167 | 3.0 × 10e7 CFU | 24.7 |
| Enterococcus faecium | 349 | 7.6 × 10e6 CFU | 23.1 |
| Streptococcus agalactiae | 624 | 3.2 × 10e7 CFU | 23.7 |
| Providencia stuartii | 25825 | 1.7 × 10e7 CFU | 30.3 |
| Stretococcus bovis | 9809 | 1.3 × 10e7 CFU | 21.9 |
| Citrobacter freundii | 6750 | 2.8 × 10e7 CFU | 29.8 |
| Aeromonas hydrophila | 7966 | 3.3 × 10e6 CFU | 29.9 |
| Porphyromonas asaccharolytica | 25260 | 9.8 × 10e6 CFU | 24.1 |
| Veillonella sp. | 10790 | 6.5 × 10e6 CFU | 23.9 |
| Peptostreptococcus prevoti | 9321 | 1.1 × 10e6 CFU | 23.5 |
| Actinomyces israeli | 10049 | 1.9 × 10e6 CFU | 36.3 |
| Listena monocytogenes | 13932 | 2.2 × 10e5 CFU | 25.1 |
| Enterobacter aerogenes | 13048 | 2.9 × 10e6 CFU | 28.1 |
| Mobiluncus curtisii subspecies curtisii | 35241 | 2.4 × 10e6 CFU | 27.7 |
| Serratia marcescens | 60 | 2.8 × 10e5 CFU | 31.0 |
| Xanthomonas maltophilia (P. maltophilia) | 12741 | 2.2 × 10e6 CFU | 25.3 |
| Streptomyces griseus subspecies somaliensis | 19437 | 1.5 × 10e6 CFU | 22.4 |
| Pasteurella multocida | 6529 | 5.4 × 10e6 CFU | 24.2 |
| Corynebacterium jeikeium | 43734 | 1.7 × 10e7 CFU | 22.1 |
| Staphylococcus epidermidis | 146 | 7.2 × 10e6 CFU | 22.2 |
| Corynebacterium renale | 19412 | 7.0 × 10e7 CFU | 25.7 |
| F. nucleatum | 25586 | 1.1 × 10e6 CFU | 22.2 |
| Salmonella cholerasius serotype enteritidis | 4931 | 1.7 × 10e7 CFU | 27.8 |
| Staphylococcus aureus subspecies aureus | 4012 | 7.0 × 10e5 CFU | 21.9 |
| Gardnerella vaginalis | 14018 | 5.4 × 10e6 CFU | 24.2 |
| B. fragilis | 25285 | 3.2 × 10e6 CFU | 21.8 |
| Proteus vulgaris | 6059 | 9.8 × 10e6 CFU | 20.2 |
| Klebsiella pneumoniae subspecies pneumoniae | 132 | 1.7 × 10e7 CFU | 26.3 |
| Prevotella denticola | 33184 | 7.4 × 10e6 CFU | 26.3 |
| Corynebacterium renale | 10848 | 2.0 × 10e6 CFU | 26.7 |
| Escherichia coli | 26 | 2.5 × 10e7 CFU | 24.8 |
| C. neoformans | 14116 | 1.1 × 10e6 CFU | 20.6 |
| Fusobacterium necrophorum | 25286 | 8.7 × 10e5 CFU | 21.4 |
| Streptococcus pyogenes | 4543 | 2.8 × 10e7 CFU | 23.0 |
| Haemophilus parainfluenzae | 7901 | 2.7 × 10e7 CFU | 20.5 |
| Neisseria gonorrhoeae | 19424 | 7.5 × 10e6 CFU | 215.4 |
| Actinomyces meyeri | 35568 | 2.2 × 10e6 CFU | 20.9 |
| Klebsiella pneumoniae subspecies ozaenae | 11296 | 4.0 × 10e6 CFU | 26.4 |
| Enterobacter cloacae | 222 | 3.3 × 10e6 CFU | 29.1 |
| Prevotella buccalis (ID is P. oralis) | 35310 | 9.8 × 10e5 CFU | 23.4 |
| Peptostreptococcus magnus | 14955 | 2.2 × 10e6 CFU | 21.7 |
| Legionella pneumophilia | 33152 | 1.2 × 10e6 CFU | 21.2 |
| Legionella pneumophiha* | ND | 1.0 × 10e7 DNA copies/reaction | 22.5 |
| Chlamydia pneumoniae* | ND | 7.6 × 10e6 DNA copies/reaction | 24.7 |
| Chlamydia trachomatis* | ND | ND | 21.3 |
| Neisseria gonorrhoeae* | ND | ND | 22.2 |
| Calf Thymus DNA* (Negative Control) | NA | 150 ng DNA | 46.1~ |
| M. pneumoniae, FH* (Positive Control) | 15531 | 10 molecules of DNA | 1404.7 |

*DNA purified as in Example 2; ND = Not Determined; NA = Not Applicable; ~3 aberrant values not included in calculation of average.

Example 5

Comparison of *M. pneumoniae* Detection by OH-PCR and Culture

A. Detection of *M. pneumoniae* in Throat Swab and Nasopharyngeal Swab Samples Using the Rep 5 Primer/Probe Set and Culture Eighteen paired throat swab and nasopharyngeal swab samples obtained from patients were tested for *M. pneumoniae* by traditional culture methodology and compared to *M. pneumoniae* detection using Rep 5 primers (SEQ ID NO 2 and SEQ ID NO 3) and Rep 5 detection probe (SEQ ID NO 5) as described in Example 1. Two throat swabs and two nasopharyngeal swabs were done per patient; one swab was used for culture and the other swab for OH-PCR; only throat swabs were cultured for *M. pneumoniae*. Sample DNA was isolated using the QIAgen nucleic acid purification method (QIAgen, Inc., Chatsworth, Calif.) and amplified and detected by the Rep 5 method described for the SEQ ID NO 5 probe in Example 2.A. above. Results are shown in Table 11.

TABLE 11

| Sample ID # | Cultrue | Rep 5 LCx ® rate (c/s/s) |
|---|---|---|
| 1A | – | 13 |
| 2A | + for *M. pneumoniae* | 12/1383* |
| 3A | – | 12 |
| 4A | – | 9 |
| 5A | + for *M. genitalium* | 11 |
| 6A | – | 10 |
| 7A | – | 11 |
| 8A | – | 11 |
| 9A | – | 11 |
| 10A | – | 11 |
| 11A | – | 118 |
| 12A | – | 11 |
| 13A | – | 11 |
| 14A | *C. pneumoniae* PC | 11 |
| 15A | *C. pneumoniae* PC | 83 |
| 16A | *C. pneumoniae* PC | 13 |
| 17A | *M. pneumoniae* PC | 1115 |
| 18A | *M. pneumornae* PC | 1293 |
| 19A | + | 914 |
| 20A | – | 12 |
| 21A | – | 11 |
| 22A | – | 11 |
| 1B | ND | 12 |
| 2B | ND | 10 |
| 3B | ND | 16 |
| 4B | ND | 11 |
| 5B | ND | 14 |
| 6B | ND | 15 |
| 7B | ND | 12 |
| 8B | ND | 14 |
| 9B | ND | 13 |
| 10B | ND | 17 |
| 11B | ND | 16 |
| 12B | ND | 17 |

TABLE 11-continued

| Sample ID # | Cultrue | Rep 5 LCx ® rate (c/s/s) |
|---|---|---|
| 13B | ND | 12 |
| 14B | C. pneumoniae PC | 11 |
| 15B | C. pneumoniae PC | 11 |
| 16B | M. pneumoniae PC | 1358 |
| 17B | M. pneumoniae PC | 1371 |
| 18B | M. pneumoniae PC | 1291 |
| 19B | ND | 403 |
| 20B | ND | 11 |
| 21B | ND | 12 |
| 22B | ND | 12 |

(PC = Positive Control; ND = Not Determined; *Retest of culture swab.)

In Table 11 above, 'A' samples were from throat swabs and 'B' samples were from nasal swabs. Samples 14A/B, 15A/B and 16A were ten-fold serial dilutions of 1.25 ng/ml of Chlamydia pneumoniae DNA, with 14A being the initial dilution, followed by 14B, 15A, 15B and 16A. None of these were detected using the M. pneumoniae Rep 5 primer/probe set. As further indication of the specificity of these primers and probes for M. pneumoniae, patient 5 was found to be culture positive for M. genitalium and was not detected as positive by the M. pneumoniae primer/probe set.

Samples 16B, 17A/B and 18A/B were ten-fold serial dilutions of 1.25 ng/ml of M. pneumoniae DNA, with 16B being the initial dilution, followed by 17A, 17B, 18A and 18B. All five of these samples were detected using the M. pneumoniae Rep 5 primer/probe set. Patient 19 was culture positive for M. pneumoniae and was also detected as positive by OH-PCR. The throat swab from patient 2 was culture positive for M. pneumoniae but the swab used for PCR testing gave a negative result. However, when the swab that had given the positive culture result was tested by OH-PCR, M. pneumoniae was detected. Therefore, the initial discrepant result was due to differences in swab sampling and was not a false negative result by the OH-PCR test. Thus the results using the Rep 5 M. pneumoniae primer/probe set showed concordance with standard culture for detection of M. pneumoniae in all patient samples tested.

B. OH-PCR and Culture Detection of M. pneumoniae in Patient Samples Four negative patient samples were spiked with M. pneumoniae DNA and tested with paired throat and nasopharyngeal swab samples from one patient found to be culture positive for M. pneumoniae using Rep 5 primers (SEQ ID NO 2 and SEQ ID NO 3) and Rep 5 detection probe (SEQ ID NO 5) or SDC1 primers (SEQ ID NO 10 and SEQ ID NO 11) and SDC1 detection probe (SEQ ID NO 12) as described in Example 1. Sample DNA was isolated using the QIAgen nucleic acid purification method and amplified and detected by the Rep 5 and SDC1 methods as in Example 2.A. for the SEQ ID NO 5 probe and Example 2.B. for the SEQ ID NO 12 probe respectively. Purified M. pneumoniae from strain M129 was used as a positive control and calf thymus DNA was used as a negative control (NC); all controls were tested in triplicate. Results are shown in Table 12.

TABLE 12

| Sample # | Rep 5 LCx ® rate (c/s/s) | SDC1 LCx ® rate (c/s/s) |
|---|---|---|
| 17 | 1033 | 1726 |
| 34 | 1347 | 1906 |
| 35 | 1372 | 1932 |
| 36 | 510 | 1343 |
| 59 | 1264 | 1850 |
| 63 | 767 | 910 |
| Calf Thymus DNA (NC) | 25 | 19 |
| M. pneumoniae, M129 (1 mol of DNA) | 1165 | 1118 |
| M. pneumoniae, M129 (10 mol of DNA) | 1203 | 1658 |

(mol of DNA = molecules of DNA)

Samples 17, 34, 35 and 36 were from patients previously found negative for M. pneumoniae into which M. pneumoniae DNA was added. Sample 59 was an M. pneumoniae culture positive throat swab and sample 63 an M. pneumoniae nasal swab from the same patient. All samples were correctly identified as positive for M. pneumoniae by both Rep 5 and SCD1 M. pneumoniae primer/probe sets using OH-PCR on the LCx.

While the invention has been described in detail and with reference to specific embodiments, it will be apparent to one skilled in the art that various changes and modifications may be made to such embodiments without departing from the spirit and scope of the invention.

What is claimed is:

1. An oligonucleotide primer or probe, said primer or probe selected from the group consisting of: SEQ ID NO 2, SEQ ID NO 3, SEQ ID NO 4, SEQ ID NO 5, SEQ ID NO 6, SEQ ID NO 7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, SEQ ID NO 26, and combinations thereof.

2. The combination of oligonucleotides of claim 1 selected from the group consisting of: SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 10 and 12; SEQ ID NOs. 10 and 13; SEQ ID NOs. 10 and 14; SEQ ID NOs. 10, 11 and 12; SEQ ID NOs. 10, 11 and 13; SEQ ID NOs. 10, 11 and 14; SEQ ID NOs. 10, 11, 12, and 13; SEQ ID NOs. 10, 11, 12, 13 and 14; SEQ ID Nos. 11 and 17; SEQ ID NOs. 11 and 18; SEQ ID NOs. 11 and 19; SEQ ID NOs. 10, 11 and 17; SEQ ID NOs. 10, 11 and 18; SEQ ID NOs. 10, 11 and 19; SEQ ID NOs. 10, 11, 17, and 18; SEQ ID NOs. 10, 11, 17, 18 and 19; SEQ ID NOs. 21 and 23; SEQ ID NOs. 22 and 26; SEQ ID NOs. 21, 22 and 23; SEQ ID NOs. 21, 22 and 26; and SEQ ID NOs. 21, 22, 23 and 26.

3. A method of detecting the presence of *M. pneumoniae* in a test sample comprising the steps of:
   a) contacting said test sample with an oligonucleotide of claim 1; and
   b) detecting hybridization between said oligonucleotide and a *M. pneumoniae* target sequence as an indication of the presence of *M. pneumoniae* in said test sample.

4. The method of claim 3 wherein said oligonucleotide is labeled.

5. A method for detecting the presence of *M. pneumoniae* in a test sample comprising the steps of:
   a) forming a reaction mixture comprising nucleic acid amplification reagents, a test sample containing a *M. pneumoniae* target sequence, and at least one primer and one probe oligonucleotide selected from the group consisting of SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 10 and 12; SEQ ID NOs. 10 and 13; SEQ ID NOs. 10 and 14; SEQ ID NOs. 10, 11 and 12; SEQ ID NOs. 10, 11 and 13; SEQ ID NOs. 10, 11 and 14; SEQ ID NOs. 10, 11, 12, and 13; SEQ ID NOs. 10, 11, 12, 13 and 14; SEQ ID Nos. 11 and 17; SEQ ID NOs. 11 and 18; SEQ ID NOs. 11 and 19; SEQ ID NOs. 10, 11 and 17; SEQ ID NOs. 10, 11 and 18; SEQ ID NOs. 10, 11 and 19; SEQ ID NOs. 10, 11, 17, and 18; SEQ ID NOs. 10, 11, 17, 18 and 19; SEQ ID NOs. 21 and 23; SEQ ID NOs. 22 and 26; SEQ ID NOs. 21, 22 and 23; SEQ ID NOs. 21, 22 and 26; SEQ ID NOs. 21, 22, 23 and 26; and homologs thereof; and
   b) subjecting said mixture to annealing and extension conditions to generate at least one nucleic acid sequence complementary to said target sequence;
   c) hybridizing said probe to said nucleic acid complementary to said target sequence so as to form a hybrid comprising said probe and said nucleic acid; and
   d) detecting said hybrid as an indication of the presence of *M. pneumoniae* in said sample.

6. The method of claim 5 wherein said probe is labeled.

7. The method of claim 5 wherein said probe is labeled with a capture label and said primer is labeled with a detection label.

8. The method of claim 5 wherein said probe is labeled with a detection label and said primer is labeled with a capture label.

9. A kit comprising:
   a) an oligonucleotide selected from the group consisting of SEQ ID NO 2, SEQ ID NO 3, SEQ ID NO 4, SEQ ID NO 5, SEQ ID NO 6, SEQ ID NO 7, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 21, SEQ ID NO 22, SEQ ID NO 23, SEQ ID NO 24, SEQ ID NO 25, SEQ ID NO 26, and combinations thereof, and
   b) amplification reagents.

* * * * *

UNITED STATES PATENT AND TRADEMARK OFFICE
CERTIFICATE OF CORRRECTION

PATENT NO. : 5,817,463
DATED : October 6, 1998
INVENTOR(S) : Mullen, et al.

It is certified that error appears in the above-identified patent and that said Letters Patent is hereby corrected as shown below:

On the title page insert the following under item [56]:

FOREIGN PATENT DOCUMENTS

|  |  | DOCUMENT NUMBER |  |  |  |  |  | PUBLICATION DATE | COUNTRY OR PATENT OFFICE | CLASS | SUBCLASS | TRANSLATION YES | NO |
|---|---|---|---|---|---|---|---|---|---|---|---|---|---|
|  |  | 9 | 4 | 2 | 1 | 6 | 7 | 5 | 09/29/94 | WO |  |  |  |  |
|  |  | 9 | 4 | 1 | 3 | 8 | 3 | 1 | 06/23/94 | WO |  |  |  |  |
|  |  | 9 | 3 | 1 | 3 | 2 | 2 | 1 | 07/08/93 | WO |  |  |  |  |
|  |  | 9 | 5 | 2 | 3 | 8 | 6 | 2 | 09/08/95 | WO |  |  |  |  |
|  |  | 5 | 2 | 7 | 6 | 9 | 6 | 0 | 10/26/93 | JP |  |  |  |  |
|  |  | 9 | 6 | 1 | 3 | 6 | 1 | 4 | 05/09/96 | WO |  |  |  |  |
|  |  |  |  |  |  |  |  |  |  |  |  |  |  |  |

Signed and Sealed this

Twenty-seventh Day of April, 1999

*Attest:*

Q. TODD DICKINSON

*Attesting Officer*  *Acting Commissioner of Patents and Trademarks*

UNITED STATES PATENT AND TRADEMARK OFFICE
CERTIFICATE OF CORRRECTION

PATENT NO. : 5,817,463
DATED : October 6, 1998
INVENTOR(S) : Carolyn R. Mullen, et al.

It is certified that error appears in the above-identified patent and that said Letters Patent is hereby corrected as shown below:

On the title page, item 56 add the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 4 | 2 | 1 | 6 | 7 | 5 | 29.09.94 | WO | | | | |
| | | 9 | 4 | 1 | 3 | 8 | 3 | 1 | 23.06.94 | WO | | | | |
| | | 9 | 3 | 1 | 3 | 2 | 2 | 1 | 08.07.93 | WO | | | | |
| | | 9 | 5 | 2 | 3 | 8 | 6 | 2 | 08.09.95 | WO | | | | |
| | | 5 | 2 | 7 | 6 | 9 | 6 | 0 | 26.10.93 | JP | | | | |
| | | 9 | 6 | 1 | 3 | 6 | 1 | 4 | 09.05.96 | WO | | | | |

U. S. PATENT DOCUMENTS

| | | PATENT NUMBER | | | | | | ISSUE DATE | PATENTEE | CLASS | SUBCLASS | TRANSLATION YES | NO |
|---|---|---|---|---|---|---|---|---|---|---|---|---|---|
| | | 5 | 0 | 2 | 6 | 6 | 3 | 6 | 06/25/91 | Baseman, et al. | | | | |

Signed and Sealed this

Nineteenth Day of October, 1999

Attest:

*Attesting Officer*

Q. TODD DICKINSON

*Acting Commissioner of Patents and Trademarks*